United States Patent
Simó Canonge et al.

(10) Patent No.: US 9,707,273 B2
(45) Date of Patent: Jul. 18, 2017

(54) PEPTIDES FOR USE IN THE TOPICAL TREATMENT OF RETINAL NEURODEGENERATIVE DISEASES, IN PARTICULAR IN EARLY STAGES OF DIABETIC RETINOPATHY AND OTHER RETINAL DISEASES IN WHICH NEURODEGENERATION PLAYS AN ESSENTIAL ROLE

(71) Applicant: FUNDACIÓ HOSPITAL UNIVERSITARI VALL D'HEBRON—INSTITUT DE RECERCA, Barcelona (ES)

(72) Inventors: Rafael Simó Canonge, Sant Cugat del Vallés (ES); Cristina Hernández Pascual, Barcelona (ES)

(73) Assignee: FUNDACIÓ HOSPITAL UNIVERSITARI VALL D'HEBRON—INSTITUT DE RECERCA, Barcelona (ES)

( * ) Notice: Subject to any disclaimer, the term of this patent is extended or adjusted under 35 U.S.C. 154(b) by 0 days.

(21) Appl. No.: 14/770,067

(22) PCT Filed: Feb. 27, 2014

(86) PCT No.: PCT/EP2014/053787
§ 371 (c)(1),
(2) Date: Aug. 24, 2015

(87) PCT Pub. No.: WO2014/131815
PCT Pub. Date: Sep. 4, 2014

(65) Prior Publication Data
US 2016/0000882 A1     Jan. 7, 2016

(30) Foreign Application Priority Data
Mar. 1, 2013 (EP) .................... 13382063

(51) Int. Cl.
| | | |
|---|---|---|
| *A61K 38/10* | (2006.01) | |
| *A61K 38/26* | (2006.01) | |
| *C07K 14/00* | (2006.01) | |
| *A61K 9/00* | (2006.01) | |
| *C07K 14/605* | (2006.01) | |

(52) U.S. Cl.
CPC ............ *A61K 38/26* (2013.01); *A61K 9/0048* (2013.01); *A61K 38/10* (2013.01); *C07K 14/605* (2013.01)

(58) Field of Classification Search
CPC ...... A61K 38/10; A61K 38/26; A61K 9/0048; C07K 14/605
USPC ........................................................ 514/11.7
See application file for complete search history.

(56) References Cited

U.S. PATENT DOCUMENTS

| | | |
|---|---|---|
| 5,424,286 A | 6/1995 | Eng |
| 2005/0215469 A1 | 9/2005 | Beeley et al. |
| 2009/0136445 A1 | 5/2009 | Wong et al. |
| 2011/0172278 A1* | 7/2011 | He ........................ C07D 249/06 514/359 |
| 2012/0021980 A1 | 1/2012 | Maggio |
| 2012/0263794 A1* | 10/2012 | Jonas ................... A61K 9/0051 424/493 |

FOREIGN PATENT DOCUMENTS

| | | |
|---|---|---|
| EP | 0944648 B1 | 3/2007 |
| WO | WO03059373 A2 | 7/2003 |
| WO | WO2007062434 A2 | 5/2007 |
| WO | WO2010130418 A2 | 11/2010 |
| WO | WO2011076368 A2 | 6/2011 |

OTHER PUBLICATIONS

Zhang et al, "Protection of exendin-4 analogue in early experimental diabetic retinopathy," Graefes Arch Clin Exp Ophthalmol, 2009, 247: 699-706.*
Exendin-4 from SIGMA, pp. 1-4. Accessed Aug. 30, 2016.*
Retinal Neurodegenerative Disease from Merck Manual, pp. 1-14. Accessed Aug. 31, 2016.*
Diabetic Retinopathy from Merck Manual, pp. 1-5. Accessed Aug. 31, 2016.*
Age-related Macular Degeneration from Merck Manual, pp. 1-8. Accessed Aug. 31, 2016.*
Glaucoma from Merck Manual, pp. 1-10. Accessed Aug. 31, 2016.*
Retinitis Pigmentosa from Merck Manual, pp. 1-3. Accessed Aug. 31, 2016.*
International Search and Written Opinion, performed by the European Patent Office for PCT Application No. PCT/EP2014/053787, mailed May 19, 2014, 11 pages, Rijswijk Netherlands.
Schmidt et al., "Neurodegenerative Diseases of the Retina and Potential for the Protection and Recovery", Current Neuropharmacology; Jun. 2008, vol. 6 No. 2, pp. 164-178; Bentham Science Publishers Ltd, .Emerate of Sharjah, United Arab Emirates.
Simó et al., "Neurodegeneration is an early event in diabetic retinopathy: therapeutic implications", British Journal of Ophthalmology J. Ophthalmol; published: Aug. 11, 2012; downloaded: Feb. 5, 2013, vol. 96, No. 10, pp. 1285-1290, BMJ Publishing Group, London, UK.
Urtti A et al., "Challenges and obstacles of ocular pharmacokinetics and drug delivery" Advanced Drug Delivery Reviews; Sep. 26, 2006; vol. 58, Issue 11, pp. 1131-1135; Elsevier B.V. , Amsterdam.

(Continued)

*Primary Examiner* — Julie Ha
(74) *Attorney, Agent, or Firm* — Peter B. Scull; Hamilton, DeSanctis & Cha LLP (57) ABSTRACT

Peptides with a sequence length from 13 to 50 amino acids, the N-terminal region of said peptides consisting in the sequence HXaa1EGTFTSDXaa2SXaa3Xaa4 (SEQ ID NO: 1) wherein: Xaa1 is an amino acid selected from alanine and glycine; Xaa2 is an amino acid selected from valine and leucine; Xaa3 is an amino acid selected from serine and lysine; Xaa4 is an amino acid selected from tyrosine and glutamine; and Hystidine is the N-terminal residue; for use in the topical treatment and/or prevention of retinal neurodegenerative diseases, in particular diabetic retinopathy are described. Pharmaceutical topical compositions for use in the topical treatment and/or prevention of these diseases are also described.

21 Claims, 4 Drawing Sheets

(56) References Cited

OTHER PUBLICATIONS

Aiello et al., "Targeting Intraocular Neovascularization and Edema—One Drop at a Time", New England Journal of Medicine; Aug. 28, 2008, vol. 359, issue 9; pp. 967-969; Massachusetts Medical Society, Waltham MA.

Zhang et al., "Intravitreal injection of exendin-4 analogue protects retinal cells in early diabetic rats", Investigative Ophthalmology & Visual Science, Jan. 2011, vol. 52, No. 1, pp. 278-285, The Association for the Research in Vision and Ophthalmology, Inc., Rockville MD.

Carrasco et al., "Lower Somatostatin Expression is an Early Event in Diabetic Retinopathy and is Associated With Retinal Neurodegeneration", Diabetes Care; Nov. 2007, vol. 30 No. 11, pp. 2902-2908; The American Diabetes Association, Alexandria VA.

Anderson et al. "Glial and endothelial blood-retinal barrier responses to amyloid-beta in the neural retina of the rat". Clinical Ophthalmology; Dec. 2008, vol. 2 No. 4, pp. 801-816, Anderson et al, publisher and licensee Dove Medical Press Ltd., Auckland, NZ.

Lambiase, Alessandro et al., Pharmacokinetics of Conjunctivally Applied Nerve Growth Factor in the Retina and Optic Nerve of Adult Rats, Investigative Ophthalmmology & Visual Science, Oct. 2005, pp. 3800-3806, vol. 46, No. 10, Association for Research in Vision and Ophthalmology, Rockville, MD, US.

Steinle, Jena, Topical Administration of Adrenergic Receptor Pharmaceutics and Nerve Growth Factor, Clinical Ophthalmology, Jun. 29, 2010, pp. 605-610, vol. 4, Clinical Ophthalmology, Dovepress, Manchester, London, UK.

Hernandez, Cristina et al., Neuroprotection in Diabetic Retinopathy, Current Diabetes Reports 2012, May 13, 2012, pp. 329-337, vol. 12, Springer, New York, NY.

Liu, Yanling et al., Pigment Epithelium-Derived Factor (PEDF) Petptide Eye Drops Reduce Inflammation, Cell Death and Vascular Leakage in Diabetic Retinopathy in INS2Akita Mice, Molecular Medicine, Oct. 2012, pp. 1387-1401, vol. 18, Feinstein Institute Press, Manhasset, NY.

* cited by examiner

SEQUENCE LISTING

<160> NUMBER OF SEQ ID NOS: 8

<210> SEQ ID NO 1
<211> LENGTH: 13
<212> TYPE: PRT
<213> ORGANISM: Artificial
<220> FEATURE:
<223> OTHER INFORMATION: N-terminal region of a peptide able to
      interact with the mammal glucagon-like peptide-1 receptor
<220> FEATURE:
<221> NAME/KEY: VARIANT
<222> LOCATION: (2)..(2)
<223> OTHER INFORMATION: X is an amino acid selected from alanine and
      glycine -continued

```
<220> FEATURE:
<221> NAME/KEY: VARIANT
<222> LOCATION: (10)..(10)
<223> OTHER INFORMATION: X is an amino acid selected from valine and
      leucine
<220> FEATURE:
<221> NAME/KEY: VARIANT
<222> LOCATION: (12)..(12)
<223> OTHER INFORMATION: X is an amino acid selected from serine and
      lysine
<220> FEATURE:
<221> NAME/KEY: VARIANT
<222> LOCATION: (13)..(13)
<223> OTHER INFORMATION: X is an amino acid selected from tyrosine and
      glutamine

<400> SEQUENCE: 1

His Xaa Glu Gly Thr Phe Thr Ser Asp Xaa Ser Xaa Xaa
1               5                   10

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 31
<212> TYPE: PRT
<213> ORGANISM: Artificial
<220> FEATURE:
<223> OTHER INFORMATION: Liraglutide; analogue of glucagon like
      peptide-1 (7-37) (GLP-1 (7-37)).
<220> FEATURE:
<221> NAME/KEY: LIPID
<222> LOCATION: (20)..(20)
<223> OTHER INFORMATION: Lysine residue (K, Lys) comprises the
      lipophilic substituent N epsilon-(gamma-glutamyl(N-alfa-
      hexadecanoyl)) attached by an amide link to the amino group of
      the lysine side chain

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 4
<211> LENGTH: 39
<212> TYPE: PRT
<213> ORGANISM: Artificial
<220> FEATURE:
<223> OTHER INFORMATION: Exenatide; glucagon-like peptide-1 agonist;
      synthetic version of hormone exendine-4 found in the saliva of
      the Gila monster.
<220> FEATURE:
<221> NAME/KEY: MOD_RES
<222> LOCATION: (39)..(39)
<223> OTHER INFORMATION: X is a serine residue in which the -COOH
      terminal has been replaced by a -NH2 group

<400> SEQUENCE: 4

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Pro Xaa
        35

<210> SEQ ID NO 5
<211> LENGTH: 13
<212> TYPE: PRT
<213> ORGANISM: Homo sapiens

<400> SEQUENCE: 5

His Ala Glu Gly Thr Phe Thr Ser Asp Val Ser Ser Tyr
1               5                   10

<210> SEQ ID NO 6
<211> LENGTH: 25
<212> TYPE: DNA
<213> ORGANISM: Artificial
<220> FEATURE:
<223> OTHER INFORMATION: Forward primer

<400> SEQUENCE: 6
gggtctctgg ctacataagg acaac                                           25

<210> SEQ ID NO 7
<211> LENGTH: 21
<212> TYPE: DNA
<213> ORGANISM: Artificial
<220> FEATURE:
<223> OTHER INFORMATION: Reverse primer

<400> SEQUENCE: 7
aaggatggct gaagcgatga c                                               21

<210> SEQ ID NO 8
<211> LENGTH: 44
<212> TYPE: PRT
<213> ORGANISM: Artificial
<220> FEATURE:
<223> OTHER INFORMATION: Lixisenatide; glucagon-like peptide-1 agonist;
      derived from exenatide
<220> FEATURE:
<221> NAME/KEY: MOD_RES
<222> LOCATION: (44)..(44)
<223> OTHER INFORMATION: X is a lysine residue in which the -COOH
      terminal has been replaced by a -NH2 group

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Xaa
        35                  40
```

PEPTIDES FOR USE IN THE TOPICAL TREATMENT OF RETINAL NEURODEGENERATIVE DISEASES, IN PARTICULAR IN EARLY STAGES OF DIABETIC RETINOPATHY AND OTHER RETINAL DISEASES IN WHICH NEURODEGENERATION PLAYS AN ESSENTIAL ROLE

The present invention relates to the field of medical approaches for ocular diseases that may lead to partial or total blindness. The invention provides useful tools to be applied topically into the eyes, including peptides and analogs of these peptides.

BACKGROUND ART

Retinal neurodegenerative diseases refer to retinal conditions characterized by progressive neuronal loss. Diabetic retinopathy, age-related macular degeneration, glaucoma and retinitis pigmentosa are considered retinal diseases in which neurodegeneration plays an essential role.

An in depth analysis of these diseases, their critical sites, as well as of possible ways of protection and ways leading to recovery can be extracted from Schmidt et al., "Neurodegenerative Diseases of the Retina and Potential for the Protection and Recovery", *Current Neuropharmacology*—2008, Vol. No. 6, pp.: 164-178.

Diabetic retinopathy (DR) is the most common complication of diabetes and remains the leading cause of blindness among working-age individuals in developed countries. Current treatments for DR such as laser photocoagulation, intravitreous injections of corticosteroids or anti-VEGF agents are indicated in too advanced stages of the disease and are associated with significant adverse effects.

Diabetic retinopathy (DR) has been classically considered to be a microcirculatory disease of the retina. However, there are some data which suggest that retinal neurodegeneration is an early event in the pathogenesis of DR which participates in the microcirculatory abnormalities that occur in DR as can be deduced from Simó et al. on behalf of the European Consortium for Early Treatment of Diabetic Retinopathy (EUROCONDOR). "Neurodegeneration is an early event in diabetic retinopathy: therapeutic implications", *Br. J. Ophthalmol.*—2012, vol. 96, pp. 1285-1290.

In the case of DR the neurodegeneration (loss of effective neurons) occurs at the early stages of the disease and produces functional abnormalities such as the loss of both chromatic discrimination and contrast sensitivity. These alterations can be detected by means of electrophysiological studies in diabetic patients even with less than two years of diabetes duration, that is, before microvascular lesions can be detected under ophthalmologic examination. In addition, a delayed multifocal ERG (electroretinography) implicit time (mfERG-IT) predicts the development of early microvascular abnormalities. Furthermore, neuroretinal degeneration initiates and/or activates several metabolic and signaling pathways which will participate in the microangiopathic process, as well as in the disruption of the blood-retinal barrier (a crucial element in the pathogenesis of DR).

The early stages of retinal neurodegenerative diseases or neurodegeneration associated with these pathologies are not currently treated, although they would prevent advanced lesions, such as microcirculatory problems leading to retinal neovascularization. Thus at early stages, in particular of DR, no treatment is applied and the standard follow-up of the patients is conducted.

On the other hand, when the early stages of these retinal neurodegenerative disease, in particular DR, are the therapeutic target, it would be inconceivable to recommend an aggressive treatment such as laser photocoagulation or intravitreous injections. To date, the use of eye drops has not been considered a good route for the administration of drugs addressed to preventing or arresting DR. This is because it is generally assumed that they do not reach the posterior segment of the eye (ie. the vitreous and the retina), as declared in Urtti A et al., "Challenges and obstacles of ocular pharmacokinetics and drug delivery". *Adv. Drug. Deliv. Rev.* 2006, vol. 58, pp. 1131-1135. Although there exists a little evidence that compounds administered in the cornea can reach the retina, they represent isolated cases and correspond to compounds of low molecular weight, such as those referred to in Aiello et al., "Targeting Intraocular Neovascularization and Edema—One Drop at a Time", *N. Eng. J Med*—2008, vol. 359, pp. 967-969. Aiello et al. show that in two different assays, a pyrrolidin derived compound (named TG100572, 4-chloro-3-(5-methyl-3-{[4-(2-pyrrolidin-I-ylethoxy)phenyl]amino}-1,2,4-benzotriazin-7-yl)phenol)) with the capability of acting as an inhibitor of kinases involved in neovascular generation and retinal edema, was able to reach the target in the retina once administered in the form of eye drops. Nonetheless, this small compound cannot be compared to compounds of other nature, such as peptides or proteins with high molecular weights.

Diabetes is a group of chronic diseases characterized by hyperglycemia. To prevent diabetic complications it is essential to reduce hyperglycemia using blood glucose lowering agents. Therefore, any glucose lowering drug could be theoretically beneficial to prevent or arrest diabetic complications, included DR. However, there is a lack of information regarding a direct effect of antidiabetic agents on DR independently of their action in reducing blood glucose levels. By way of example, the glucagon-like peptide 1 agonists known as exenatide (Byeta, Amylin Pharmaceuticals) and liraglutide (Victoza, Novo Nordisk) are used for treating type 2 diabetes by promoting the lowering of blood glucose levels. Moreover, it is known that these agonists give rise to an improvement in the associated diseases of metabolic syndrome such as obesity and high blood pressure. Also the document of patent application WO2007062434 discloses a pharmaceutical composition to be intranasally administered, in which the same glucagon-like peptide 1 (GLP-1) is delivered for treating metabolic syndrome and diabetic complications, including DR.

From the above, therefore, it is known that administration of such glucagon-like peptide 1 agonists also improve or attenuate DR symptoms, since the leading cause or the origin of the disease, in particular the high levels of glucose in blood, is at final instance improved. Nonetheless, these treatments are not deprived of systemic adverse effects. If, moreover, these substances have to reach the retina at therapeutic concentrations, high doses are required thus increasing the adverse effects.

One study showing neuroprotection mediated by GLP-1R activation in an in vivo model is disclosed in Zhang et al., "Intravitreal injection of exendin-4 analogue protects retinal cells in early diabetic rats", *Invest Ophthalmol Vis Sci.*—2011, vol. 52(1), pp. 278-85. The authors reported that intravitreal administration of exendin-4 (exenatide) prevented electroretinography (ERG) abnormalities and morphological features related to neurodegeneration in rats with diabetes induced by streptozotocin (STZ). However, the results in the study of Zhang et al. cannot be easily extrapolated to human DR (or to other diseases with retinal neurodegeneration). Firstly, because in the STZ-DM model the interpretation of the results might be hampered by the neurotoxic effect of STZ. Secondly, although GLP-1R expression has been found in retinas from rats it has not been previously reported in human retinas. Finally, and as above mentioned, intravitreous injections are inappropriately invasive in patients with very few if any microvascular abnormalities in fundoscopic examination.

At present, there are no specific treatments for retinal neurodegenerative diseases. In the particular case of DR, this means that there are no specific treatments for the background retinopathy or non-proliferative DR, as well as for protecting the neuroretina from damage (leading to loss of neurons). Therefore, new pharmacological treatments for the early stages of the disease, when neurodegeneration seems to be starting are needed. Early treatment of DR will be effective in reducing the progression to advanced stages needing aggressive therapies such as surgical intervention.

SUMMARY OF THE INVENTION

The inventors have found that some peptides, all of them having in common a specific sequence in the N-terminal region, as well as compositions comprising said peptides, when applied topically in the eye (i.e. in the cornea or conjunctival fornix) were able to reach the retina, despite their high molecular weight and they were also able to protect and prevent the retina from degeneration. These compounds acted as topical neuroprotectors of the retina (in particular the neuroretina, which is the part of the retina including the neurons but without the retinal pigment epithelium).

It should be emphasized that the topical administration of peptides for use according to the invention, not only reach the retina, but also achieve effective concentrations for abrogating the evolution of diabetic retinopathy.

Thus, in a first aspect the invention relates to peptides with a sequence length from 13 to 50 amino acids, the N-terminal region of said peptides consisting in the sequence:

HXaa$^1$EGTFTSDXaa$^2$SXaa$^3$Xaa$^4$ (SEQ ID NO: 1)
wherein:
Xaa$^1$ is an amino acid selected from alanine and glycine;
Xaa$^2$ is an amino acid selected from valine and leucine;
Xaa$^3$ is an amino acid selected from serine and lysine;
Xaa$^4$ is an amino acid selected from tyrosine and glutamine; and
Hystidine is the N-terminal residue;
for use in the topical treatment and/or prevention of retinal neurodegenerative diseases.

The topical treatment and/or prevention is a topical eye treatment and/or prevention, thus in the eye surface (i.e. in the cornea or conjunctival fornix), due to the fact that the peptides can reach the retina when applied topically to eyes. This applies to any of the embodiments and combination of embodiments disclosed in the present invention.

The inventors surprisingly discovered that the glucagon-like peptide 1 receptor (GLP-1 Rc) was present in human retina, and contrary to all previous assumptions, they were able demonstrate that substances of peptide nature with a molecular weight ranging from 3.35 kDa to 4.18 kDa could reach the retina when applied topically to eyes (i.e. in the cornea). Thus, the inventors propose the topical use (topical eye use) of peptides comprising from 30 to 40 aminoacids and including SEQ ID NO: 1, which sequence is considered responsible of the activation of the GLP-1 Rc, and is also present in the mammal GLP-1.

Considering the state of the art, it was unexpected that molecules of a molecular weight greater than 1 kDa would be able to reach the retina once administered topically in the corneal surface.

GLP-1 (glucagon-like peptide-1) is an endogenous insulinotropic peptide that is secreted from the L cells of the gastrointestinal tract in response to food ("incretin response"). GLP-1 by acting thorough its receptor (GLP-1Rc), has potent effects on glucose-dependent insulin secretion, insulin gene expression, islet beta-cell neogenesis, gastrointestinal motility, energy homeostasis and food intake. The GLP-1 receptor (GLP-1Rc) is a member of the peptide hormone binding class B1 (secretin-like receptors) family of seven transmembrane spanning, heterotrimeric G-protein coupled receptors (GPCRs). GLP-1Rs have a broad distribution and they are found in the pancreas, adipose tissue, muscle, heart, the gastrointestinal tract and the liver. In addition, GLP-1Rs are found throughout the central nervous system (ie. hypothalamus, striatum, brain stem, substantia nicra, and subventricular zone), and there is some evidence that GLP-1R stimulation by GLP-1 exerts neuroprotective effects in both the central and peripheral nervous systems.

Human GLP-1 is a 37 amino acid residue peptide originating from preproglucagon which is synthesized i.a. in the L-cells in the distal ileum, in the pancreas and in the brain. The human preproglucagon is identified with the UniProt database Accession Number P01275, Feb. 6, 2007; Version 3. The processing of preproglucagon to give GLP-1 (7-36) amide, GLP-1(7-37) and GLP-2 occurs mainly in the L-cells. A simple system is used to describe fragments and analogues of this peptide. Thus, for example, Gly$^8$-GLP-1 (7-37) designates a fragment (analogue) of GLP-1 formally derived from GLP-1 by deleting the amino acid residues Nos. 1 to 6 and substituting the naturally occurring amino acid residue in position 8 (Ala) by Gly. Similarly, Lys$^{34}$(N$^\epsilon$-tetradecanoyl)-GLP-1 (7-37) designates GLP-1(7-37) wherein the $\epsilon$-amino group of the Lys residue in position 34 has been tetradecanoylated.

Thus, contrary to all prejudices, the inventors have solved a long-felt need in the field of ophthalmology by providing peptides that, by means of topical administration or as ingredients of topical compositions (thus topical eye compositions) can reach the retina and exert therein a neuroprotection effect. In addition, the topical administration of these peptides limits their action to the eye and minimises the associated systemic adverse effects.

This aspect of the invention can also be formulated as the use of a peptide with a sequence length from 13 to 50 amino acids and comprising at the N-terminal region of said peptide the amino acid sequence consisting in HXaa$^1$EGTFTSDXaa$^2$SXaa$^3$Xaa$^4$ (SEQ ID NO: 1) as defined above for the manufacture of a medicament for the treatment and/or prevention of retinal neurodegenerative diseases (which means topical eye treatment and/or prevention), in particular for the treatment and/or prevention of the retina in early stages of retinal neurodegenerative diseases, in particular early stages of DR, due to the neuroprotective effect of the peptides. The present invention also relates to a method for the treatment and/or prevention of retinal neurodegenerative diseases, in particular for neuroprotection in early stages of retinal neurodegenerative diseases, in particular early stages of DR, comprising administering (meaning topically administering in the eye) a therapeutically effective amounts of a peptide with a sequence length from 13 to 50 amino acids and comprising at the N-terminal region of said peptide the amino acid sequence consisting in HXaa$^1$EGTFTSDXaa$^2$SXaa$^3$Xaa$^4$ (SEQ ID NO: 1) as defined above, together with pharmaceutically acceptable excipients and/or carriers, in a subject in need thereof, including a human.

BRIEF DESCRIPTION OF THE DRAWINGS

FIG. 2 shows the expression of the GLP-1 receptor in human tissue samples. Panel A is a bar diagram in which the relative amount of the mRNA of GLP-1 receptor has been analyzed by quantitative real-time PCR. In panel B an optical microscope image (20×) of a section of a human neuroretina clearly exposes (referenced with the bold arrow) the presence of the receptor in the photoreceptors segments (PR). "ONL" means outer nuclear layer; "INL" means inner nuclear layer; and "GCL" means ganglion cell layer, all of them being constitutive parts of the neuroretina.

FIG. 4 also related to diabetic retinopathy (DR), is a bar diagram showing the results of a TUNEL assay. Panel A shows the percentage of TUNEL (%) positive cells in the Ganglion cell layer (GCL) in diabetic mice treated with a GLP-1(7-37) analogue, which is a GLP-1R agonist (Test, T, n=10) and diabetic mice treated with vehicle (Control, C, n=10). Panel B shows the TUNEL positive immunofluorescence in the whole neuroretina from diabetic mice treated with GLP-1R agonist (T) and diabetic mice treated with vehicle (Control, C). A.U.: arbitrary units. Results are mean±SD. * p<0.05.

DETAILED DESCRIPTION OF THE INVENTION

For the sake of understanding, the following definitions are included.

In the sense of the invention, the term "neuroprotection" means any kind of treatment or prophylactic method that can be used in order that neurons constituting the neuroretina remain preserved and in a physiological state corresponding to the one of a health subject animal (including humans). The "neuroretina" is the part of the retina including the neurons and without the retinal pigment epithelium. Neuroretina is the responsible of the visual cycle.

The expression "neuroprotection in the early stages of diabetic retinopathy" relates to any treatment or prophylactic method carried out before advances stages of DR (pre-proliferative or proliferative DR) are established.

For "early stages of diabetic retinopathy" is to be understood as the time in which, due to the presence of diabetes, functional abnormalities can be detected in the eye (i.e. chromatic discrimination, contrast sensitivity and electroretinography abnormalities), but the pattern of microvascular changes of DR has not yet been fully established, that is, there cannot be observed the typical lesions of pre-proliferative or proliferative DR.

"Human glucagon like peptide-1 (7-36) amide (GLP-1 (7-36)amide)", and "human glucagon like peptide-1 (7-37) (GLP-1(7-37)" relate to the fragments derived from human proglucagon and comprising from amino acid 7 to 36 or from amino acid 7 to 37, respectively, of the amino acid sequence of said human proglucagon.

As "analogue of human GLP-1 (7-37)" is to be understood a peptide wherein one or more amino acid residues of the GLP-1(7-37) have been substituted by another amino acid residue and/or wherein one or more of the amino acid residues of the GLP-1(7-37) have been deleted and/or wherein one or more amino acid residues have been added to the GLP-1(7-37).

The expression "therapeutically effective amount" as used herein, refers to the amount of a compound that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

The term "pharmaceutically acceptable" as used herein pertains to compounds, materials, compositions, and/or dosage forms which are, within the scope of sound medical judgment, suitable for use in contact with the tissues of a subject (e.g. human) without significant toxicity, irritation, allergic response, or other problem or complication, commensurate with a reasonable benefit/risk ratio. Each carrier, excipient, etc., must also be "acceptable" in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio. Suitable carriers, excipients, etc. can be found in standard pharmaceutical texts, and include, as a way of example preservatives, agglutinants, humectants, emollients, and antioxidants.

The "N-terminal region" or "the N-terminus" (also known as the amino-terminus, NH2-terminus, N-terminal end or amine-terminus, all of them used herewith as interchangeable expressions) refers to the start of a protein or polypeptide terminated by an amino acid with a free amine group (—NH2). The convention for writing peptide sequences is to put the N-terminus on the left and write the sequence from N- to C-terminus. When the protein is translated from messenger RNA, it is created from N-terminus to C-terminus.

For "N-terminal residue" is to be understood the residue in a peptide that has an amino group that is free, or at least not acylated by another amino-acid residue (it may, for example, be acylated or formylated), is called N-terminal; it is at the N-terminus. The residue that has a free carboxyl group, or at least does not acylate another amino-acid residue, (it may, for example, acylate ammonia to give —NH—CHR—CO—NH2), is called C-terminal.

As above exposed, the inventors propose for the first time a therapeutically approach for retinal neurodegenerative diseases (retinal diseases in which neurodegeneration plays an essential role) that, apart of being non-aggressive, is useful in the treatment of the early stages of these diseases, and in particular in the treatment of the early stages of DR.

In a particular embodiment, the peptide for use in the topical treatment and/or prevention according to the invention has a sequence length from 30 to 50 amino acids.

Another particular embodiment is a peptide with a sequence length from 30 to 40 amino acids, the N-terminal region of said peptide consisting in the sequence:

HXaa$^1$EGTFTSDXaa$^2$SXaa$^3$Xaa$^4$ (SEQ ID NO: 1)
  wherein:
  Xaa$^1$ is an amino acid selected from alanine and glycine;
  Xaa$^2$ is an amino acid selected from valine and leucine;
  Xaa$^3$ is an amino acid selected from serine and lysine;
  Xaa$^4$ is an amino acid selected from tyrosine and glutamine; and
  hystidine is the N-terminal residue;
for use in the topical treatment and/or prevention of a retinal neurodegenerative disease.

Yet in another particular embodiment, the peptide has a sequence with a length from 13 to 40 amino acids.

This means that any of the peptides with any of the specified sequence length may be used in the manufacture of a medicament for the treatment and/or prevention of retinal neurodegenerative diseases (which means topical eye treatment and/or prevention), in particular for the treatment and/or prevention of the retina in early stages of retinal neurodegenerative diseases, in particular early stages of DR. Thus, the invention also relates in particular embodiments to methods for the treatment and/or prevention of retinal neurodegenerative diseases, in particular for neuroprotection in early stages of retinal neurodegenerative diseases, in particular early stages of DR, comprising administering (meaning topically administering in the eye) a therapeutically effective amounts of a peptide with any of the sequence lengths specified above.

In particular, the peptide for use in the topical treatment and/or prevention according to the invention, which means for use in the topical eye treatment and/or prevention, is for the treatment and/or prevention of retinal neurodegenerative disease selected from the group consisting of DR, age-related macular degeneration, glaucoma and retinitis pigmentosa.

In a preferred embodiment, the peptide for use in the topical treatment and/or prevention according to the invention, is for the treatment and/or prevention of DR.

Further, in another preferred embodiment, the peptide for use in the topical treatment and/or prevention according to the invention, is for the treatment and/or prevention of the early stages of DR.

In particular, at these early stages when DR is not established yet, the peptides of the invention applied topically act as neuroprotector agents of the neuroretina, thus exerting a neuroprotection effect. This means that neurons are preserved from damage and loss of function, and they are maintained in a health physiological state. The same reasoning applies with the other retinal neurodegenerative diseases. Indeed, the peptides can be used due to its neuroprotective properties.

Figure 1:
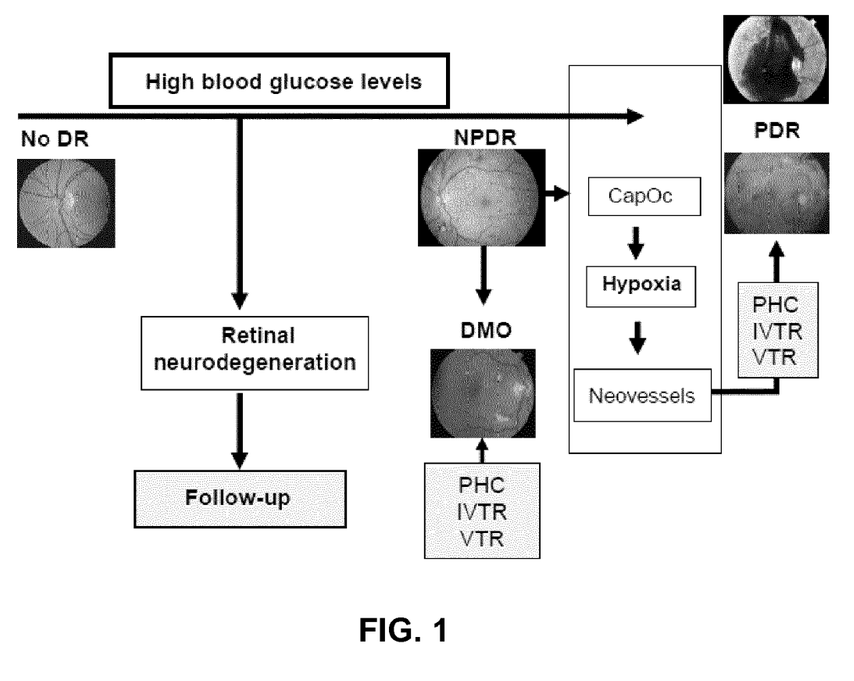
FIG. 1 represents a schematic view of the progression of the particular retinal neurodegenerative disease, diabetic retinopathy (DR) (early stages and late stages) and of the therapeutical approaches employed in each of the stages according to the prior art. The horizontal arrow represents time (in arbitrary units), along which increased levels of glucose in blood are detectable (diabetes or High blood glucose levels). "No DR" means normal ocular inspection (with no microaneurysms, microhemorrages or exudates); "NPDR" means non-proliferative diabetic retinopathy; "DMO" means diabetic macular edema; "CapOc" means capillary Occlusion, "PDR" means proliferative diabetic retinopathy; "PHC" means photocoagulation; "IVTR" means intravitreous injection; and "VTR" means vitrectomy. The term neovessels is referring to the new formed vascular vessels.

An schematic representation of the diabetic retinopathy development can be seen in FIG. 1. Briefly, the metabolic pathways triggered by hyperglycemia, and hyperglycemia itself, lead to DR but a period of at least five years is required before DR can be diagnosed under ophthalmoscopic examination. The first stage that can be seen is background retinopathy or non-proliferative diabetic retinopathy (NPDR) (which is constituted by microaneurysms, microhemorrhages and hard exudates). At this stage there is no specific treatment but the standard follow-on of the diabetic subject. From this stage the natural history of the disease can follow two directions that do not exclude the other. One of them is the development of clinically significant diabetic macular edema (DMO) in which the most important pathogenic element is the breakdown of the blood retinal barrier (BRB). This way is more frequent in type 2 diabetic patients. The other direction is towards proliferative diabetic retinopathy (PDR), which is more frequent in type 1 diabetes. In this later setting capillary occlusion plays an essential role generating an imbalance between angiogenic and antiangiogenic factors, which finally stimulates neovascularization (the hallmark of PDR). However, even before NPDR could be detected in the ophthalmologic examination, retinal neurodegeneration does exist. As indicated in FIG. 1, aggressive treatments are performed when DMO and PDR is established. Said treatments include photocoagulation (PGC), intravitreous injections of corticosteroids and/or anti vascular endothelial growing factors (IVTR), and vitrectomy (VTR).

With the peptides for use in the topical treatment and/or prevention of DR according to the invention, some of these aggressive treatments can be avoided if in the early stages of the disease, when functional abnormalities can be detected (i.e. chromatic discrimination, contrast sensitivity and electroretinography abnormalities), the subject receives compounds aiding the neuroprotection of the retina. So that, if the retina is protected from the consequences of chronic blood glucose levels, major complications can be minimized, or even never appear with the real improvement of life quality of diabetic patients. The topical administration to eye of the peptides represents a real advantage, avoiding further aggressive treatments.

In an embodiment, the peptide for use in the treatment and/or prevention of retinal neurodegenerative diseases, in particular of DR, has a sequence length selected from the group consisting of 31, 32, 33, 34, 37, 36, 37, 38, and 39 amino acids. In another embodiment the sequence length is selected from 14, 15, 16, 17, 18, 19, 20, 21, 22, 23, 24, 25, 26, 27, 28, 29, 30, 31, 32, 33, 34, 37, 36, 37, 38, 39, 40, 41, 42, 42, 44, 45, 46, 47, 48 and 49 amino acids.

In an embodiment of the invention, the peptides for use in the topical (ocular) treatment and/or prevention of retinal neurodegenerative diseases, are those comprising at the N-terminal end the amino acid sequence consisting in SEQ ID NO: 1 in which $Xaa^1$ is alanine, $Xaa^2$ is valine, $Xaa^3$ is serine and $Xaa^4$ is tyrosine. That is, they comprise the amino acid sequence SEQ ID NO: 5 (HAEGTFTSDVSSY). These peptides are, in particular, for the topical treatment and/or prevention of DR, which is for the topical eye treatment and/or prevention of DR In another embodiment the peptide for use according to the invention is a mammal glucagon-like peptide-1. This peptide includes at its N-terminal end (N-terminal region) the sequence identified as SEQ ID NO: 5, which is maintained in most mammals, such as humans, pigs and monkeys. In addition, this is the sequence which is mostly recognized by the GLP-1Rc.

Thus, in a preferred embodiment, the peptide for use in the topical (ocular) treatment and/or prevention of retinal neurodegenerative diseases (i.e. DR) consists in the human glucagon-like peptide-1 of amino acid sequence SEQ ID NO: 2, corresponding to HAEGTFTSDVSSYLEGQAAKE-FIAWLVKGRG, and variations of this human peptide. The variations relate to mutations between individuals, meanwhile these mutations do not affect the interaction with the GLP-1 Rc, and do not deprive the peptide of acting through this receptor (in particular as agonist or activator of the subsequent signaling pathway leading to neuroprotection or to the lowering of blood glucose levels). By "mutations" is to be understood any deletion of one or two amino acids, and a substitution or addition of a conservative amino acid.

In another embodiment, the peptide for use according to the invention is one with the amino acid sequence SEQ ID NO: 3 (HAEGTFTSDVSSYLEGQAAKEFIAWLVRGRG), wherein the lysine (K) comprises the lipophilic substituent $N^\epsilon$-($\gamma$-glutamyl($N^\alpha$-hexadecanoyl)) attached by an amide link to the amino group of the lysine side chain. That is, the peptide consists in SEQ ID NO: 3.

SEQ ID NO: 3 corresponds to the active principle known as liraglutide (also named $Arg^{34}Lys^{26}(N^\epsilon$-($\gamma$-glutamyl($N^\alpha$-hexadecanoyl)))-GLP-1 (7-37)), which is considered an analogue of the GLP-1 (7-37) of those that comprise a lipophilic substituent in at least one amino acid, said lipophilic substituent being an acyl group of a straight-chain or branched alkane $\alpha,\omega$-dicarboxylic acid. Preferred acyl groups in these analogues of GLP-1 (7-37) are selected from the group comprising $HOOC(CH_2)mCO$—, wherein m is from 4 to 38, preferably from 4 to 24, the more preferred being selected from the group comprising $HOOC(CH_2)_{14}CO$—, $HOOC(CH_2)_{16}CO$—, $HOOC(CH_2)_{18}CO$—, $HOOC(CH_2)_{20}CO$— and $HOOC(CH_2)_{22}CO$—.

Thus, the present invention also encompasses mammal Glucagon like peptide-1 (7-37) or analogues thereof for use in the topical (ocular) treatment of retinal neurodegenerative diseases, in particular of DR, wherein the analogue of Glucagon like peptide-1 (7-37) is a peptide that comprises at least one of the following modifications:

a) a deletion of at least one amino acid residue of the Glucagon like peptide-1 (7-37);
b) at least the substitution of one amino acid residue of the Glucagon like peptide-1 (7-37) by another amino acid residue; and
c) the addition of at least one amino acid residue at the C-terminal end of the Glucagon like peptide-1 (7-37), meanwhile they include at the N-terminal region the amino acid sequence SEQ ID NO: 1. Said analogues are, in addition peptide agonists of the human Glucagon like peptide-1 receptor, being able to stimulate formation of cAMP when tested in front of the receptor.

In particular mammal Glucagon like peptide-1 (7-37) or analogues thereof are usable in the treatment and/or prevention of retinal neurodegenerative diseases, in particular of DR, in an early stage of the disease. The peptides, when applied topically in the eye, act as neuroprotector agents in the early stages (avoiding neurodegeneration in case of preventive treatment).

Examples of analogues of GLP-1(7-37) also for use in the treatment and/or prevention of retinal neurodegenerative diseases, in particular of DR, include a part of liraglutide, $Lys^{26}(N^\epsilon$-(tetradecanoyl)-GLP-1 (7-37); $Lys^{34}(N^\epsilon$-(tetradecanoyl)-GLP-1 (7-37); $Lys^{26,34}bis(N^\epsilon$-(tetradecanoyl)-GLP-1 (7-37); $Lys^{26}(N^\epsilon$-(tetradecanoyl)$Arg^{34}$-GLP-1 (7-37); $Gly^8Arg^{26,34}Lys^{35}(N^\epsilon$-(tetradecanoyl)-GLP-1 (7-37); $Arg^{26,34}Lys^{36}(N^\epsilon$-(tetradecanoyl))-GLP-1 (7-37); $Lys^{26,34}bis(N^\epsilon$-($\omega$-carboxynonadecanoyl))-GLP-1 (7-37); $Arg^{34}Lys^{26}(N^\epsilon$-($\omega$-carboxynonadecanoyl))-GLP-1 (7-37); $Arg^{34}Lys^{26}(N^\epsilon$-($\omega$-carboxyheptadecanoyl))-GLP-1 (7-37); $Arg^{26,34}Lys^{36}(N^\epsilon$-($\omega$-carboxyheptadecanoyl))-GLP-1 (7-37); $Arg^{26,34}Lys^{36}(N^\epsilon$-($\omega$-carboxyundecanoyl))-GLP-1 (7-37); $Lys^{26,34}bis(N^\epsilon$-($\omega$-carboxyundecanoyl))-GLP-1 (7-37); $Arg^{34}Lys^{26}(N^\epsilon$-($\omega$-carboxyundecanoyl))-GLP-1 (7-37); $Arg^{34}Lys^{26}(N^\epsilon$-($\omega$-carboxyheptanoyl))-GLP-1 (7-37); $Arg^{26,34}Lys^{36}(N^\epsilon$-($\omega$-carboxyheptanoyl))-GLP-1 (7-37); $Lys^{26,34}bis(N^\epsilon$-($\omega$-carboxyheptanoyl))-GLP-1 (7-37); $Arg^{34}Lys^{26}(N^\epsilon$-($\omega$-carboxypentadecanoyl))-GLP-1 (7-37); $Arg^{34}Lys^{26}(N^\epsilon$-(lithocholyl))-GLP-1 (7-37); $Lys^{26,34}bis(N^\epsilon$-($\omega$-carboxytridecanoyl))-GLP-1 (7-37); $Lys^{26,34}bis(N^\epsilon$-($\gamma$-glutamyl($N^\alpha$-tetradecanoyl)))-GLP-1 (7-37); $Lys^{26,34}bis(N^\epsilon$-($\gamma$-glutamyl($N^\alpha$-hexadecanoyl)))-GLP-1 (7-37); $Arg^{34}Lys^{26}(N^\epsilon$-($\gamma$-glutamyl($N^\alpha$-tetradecanoyl)))-GLP-1 (7-37)

All these analogues are widely disclosed in the patent document EP0944648 (Novo Nordisk), wherein examples of its synthesis are also included. Most of them are obtained by recombinant technology performed in microorganisms, as well as by chemical synthesis.

In another embodiment, the peptides for use in the topical (ocular) treatment and/or prevention of retinal neurodegenerative diseases, are those comprising at the N-terminal region the amino acid sequence consisting in SEQ ID NO: 1 in which $Xaa^1$ is glycine, $Xaa^2$ is leucine, $Xaa^3$ is lysine, and $Xaa^4$ is glutamine. The peptides are, in particular, for the topical treatment and/or prevention of DR.

In another embodiment the peptide for use in the treatment and/or prevention of a retinal neurodegenerative disease, in particular DR, consists in, or is the one with the amino acid sequence SEQ ID NO: 4 (HGEGTFTSDL-SKQMEEEAVRLFIEWLKNGGPSSGAPPPXaa$^5$), wherein $Xaa^5$ is a serine residue in which the terminal —COOH has been replaced by a —NH2 group. This SEQ ID NO: 4 corresponds to the active principle known as exenatide (Amylin Pharmaceuticals). The compound can be obtained by solid chemical synthesis or using the DNA recombinant technology in microorganisms, as exposed in the document U.S. Pat. No. 5,424,286.

In another embodiment the peptide for use in the treatment and/or prevention of a retinal neurodegenerative disease, in particular DR, consists in, or is the one with the amino acid sequence SEQ ID NO: 8 (HGEGTFTSDL-SKQMEEEAVRLFIEWLKNGGPSSGAPPSKKKK-KXaa$^6$), wherein $Xaa^6$ is a lysine residue in which the —COOH terminal has been replaced by a —NH$_2$ group. This SEQ ID NO: 8 corresponds to the active principle known as lixisenatide (Sanofi-Aventis). The compound can be obtained by solid chemical synthesis (Merifield solid-phase methodology). The product is widely disclosed in the patent document U.S. Pat. No. 6,528,486.

All these peptides of the invention with a length from 13 to 50 amino acids, particularly from 30 to 50, or from 30 to 40 and comprising at the N-terminal end (N-terminal region) the amino acid sequence consisting in SEQ ID NO: 1, as well as any peptide defined as analogue of the GLP-1(7-37), are agonists of the GLP-1Rc. Indeed it is considered that this SEQ ID NO: 1 is at least part of the amino acid sequence that interacts with the GLP-1Rc. As exemplified below, all of them may be topically used in the treatment and/or prevention of a retinal neurodegenerative disease, in particular of DR.

Thus, in a particular embodiment, the peptides for use according to the invention are agonists of the GLP-1 Rc.

The determination of the agonist activity for a particular peptide can be tested by means of an assay in which stimulation of cAMP formation in a cell line which is expressing the cloned human GLP-1Rc. An example of such an assay is derivable from the patent document EP0944648 (Novo Nordisk).

Briefly, the EC50 of a particular peptide is calculated from a dose-response curve determined using Baby hamster kidney (BHK) cells expressing the human pancreatic GLP-1Rc. The plasma membranes of the cells are prepared by homogenisation in buffer (10 mmol/l Tris-HCl and 30 mmol/l NaCl pH 7.4, containing, in addition, 1 mmol/l dithiothreitol, 5 mg/l leupeptin (Sigma, St. Louis, Mo., USA), 5 mg/l pepstatin (Sigma, St. Louis, Mo., USA), 100 mg/l bacitracin (Sigma, St. Louis, Mo., USA), and 16 mg/l aprotinin (Novo Nordisk NS, Bagsvaerd, Denmark)). The homogenate is then centrifuged on top of a layer of 41 w/v % sucrose. The white band between the two layers is diluted in buffer and centrifuged. The assay can be carried out in 96-well microtiter plates in a total volume of 140 µl. The buffer used can be 50 mmol/l Tris-HCl, pH 7.4 with the addition of 1 mmol/l EGTA, 1.5 mmol/l MgSO4 1.7 mmol/l ATP, 20 mM GTP, 2 mmol/l 3-isobutyl-1-methylxanthine, 0.01 Tween-20 and 0.1% human serum albumin (Reinst, Behringwerke AG, Marburg, Germany). Compounds to be tested for agonist activity are dissolved and diluted in buffer, added to the membrane preparation and the mixture is incubated for 2 h at 37° C. The reaction is stopped by the addition of 25 µl of 0.05 mol/l HCl. Samples are diluted 10 fold before analysis for cAMP by a scintillation proximity assay (RPA 538, Amersham, UK).

A peptide is then considered an agonist if under these conditions the EC50 (pM) is at least the one of GLP-1 (7-37), that is from at least 55 pM or, preferably, from at least 60 pM.

The protection of retinal neurodegeneration detected by means of several ophthalmological examinations represents a good approach for treating DR before vascular abnormalities are developed. In the early stages of DR neurodegeneration exists (which can be detected by the loss of both chromatic discrimination and contrast sensitivity, glial activation and apoptosis of neural cells). The peptides for topical administration (topical administration to the eye) of the invention are useful in these early stages when no treatment is indicated and only the follow-up is recommended until more advances stages of DR are established (clinically significant diabetic macular edema and/or proliferative diabetic retinopathy).

Treatment in the early stages of DR has the real advantage that further complications are avoided, namely microaneurysms, microhemorrhages, hard exudates, neovascularization, capillary occlusion, and breakdown of the blood retinal barrier (BRB).

In another embodiment, the peptide for use according to the invention, is an ingredient (component) of a pharmaceutical topical composition, said composition comprising at least one peptide as above disclosed and any pharmaceutically acceptable carriers and/or excipients. Thus, the invention relates also to a pharmaceutical topical composition for use in the topical treatment and/or prevention of retinal neurodegenerative diseases, in particular of diabetic retinopathy, which comprises at least on peptide as defined above. Particular and/or excipients relate to water, saline buffers, and mixtures of water in oil or oil in water. Particular excipients are selected from preservatives, agglutinants, humectants, emollients, and antioxidants.

Preferred pharmaceutical topical compositions are selected from the group consisting of solutions (for example eye drops), creams, lotions, unguents, emulsions, aerosols and non-aerosol sprays, gels, ointments and suspensions. As above exposed, the pharmaceutical topical compositions are to be understood as topical eye compositions.

Additionally, the compositions of the present invention may contain other ingredients, such as fragrances, colorants, and other components known in the state of the art for use in topical formulations.

Topical compositions of the present invention can be prepared according to methods well known in the state of the art. The appropriate excipients and/or carriers, and their amounts, can readily be determined by those skilled in the art according to the type of formulation being prepared.

In a preferred embodiment, the topical composition of the invention is a solution in the form of eye drops, also named eye drop solution. The administration of the peptides in the form of eye drops implies the great advantage of being easy to be used by the subject in need thereof, and non-discomfortable.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1. GLP-1-Rc is Expressed in Human Retinas

It is known that the main features of retinal neurodegeneration (apoptosis and glial activation) are already present in the retinas of diabetic donors without any microcirculatory abnormalities in the ophthalmoscopic examinations performed during the year before death (Carrasco et al., "Lower Somatostatin Expression Is an Early Event in Diabetic Retinopathy and Is Associated With Retinal Neurodegeneration", *Diabetes Care*—2007, Vol. No. 30, pp.: 2902-2908). Therefore, a normal ophthalmoscopic examination does not exclude the possibility that retinal neurodegeneration is already present in the diabetic eye.

In the present study the inventors wanted to detect if in the human retina GLP-1 receptor (GLP-1Rc) was expressed.

Eight human postmortem eyes were obtained from eight diabetic and eight non-diabetic donors (age: 66.9±5.4 years). The time elapsed from death to eye enucleation was less than 4 h. After enucleation, one eye of each donor was snap frozen at −80° C. and stored until assayed for mRNA. The other eye cup was fixed in 4% paraformaldehyde and embedded in paraffin for the immunohystochemical study.

All ocular tissues were used in accordance with applicable laws and with the Declaration of Helsinki for research involving human tissue. In addition this study was approved by the ethics committee of the Vall d'Hebron Hospital (Barcelona—Spain).

Neuroretina and retinal pigment epithelium (RPE) were harvested under the microscopic dissection of isolated eye cups from donors. The neuroretina and RPE from each eye were ground to powder in liquid nitrogen using a mortar. Tissue was homogenized by QIAshredder spin column (Quiagen, Hilden, Germany) and mRNA was extracted from tissue using RNeasy Micro Kit (Quiagen, Hilden, Germany) according to the manufacturer's instructions. mRNA concentration and integrity was determined by RNA nano Lab Chip Kit Bioanalyzer (Agilent, Palo Alto, Calif., USA). One µg of total mRNA was reverse transcribed using TaqMan® Reverse Transcription Reagents (Applied Biosystems, Roche, N.J., USA) following the manufacturer's protocol for random hexanucleotide priming. Quantitative real-time PCR (Q-RT-PCR) was performed using an ABI Prism 7000 Sequence Detection System (Perkin-Elmer Applied Biosystems; Madrid, Spain) according to the manufacturer's protocol. Levels of GLP-1Rc were assessed with the TaqMan Assays.

For an immunofluorescence assay, paraffinized eyes were serially cut to 7 µm thickness. Sections were deparaffinized with xylene and rehydrated in ethanol. Sections were then fixed and placed in antigen-retrieval solution (Dako A/S, Glostrup, Denmark) for 20 min at 95° C. Sections were then incubated for 1 h with 1% BSA in 0.3% Triton X-100 in PBS to block unspecific binding of the antibodies and then incubated overnight at 4° C. with a specific primary antibody to human GLP-1Rc (Abcam, Cambridge, UK). Sections were washed before being incubated with Alexa Fluor® 488 (Molecular Probes, Eugene, Oreg.) secondary antibody at room temperature for 1 h. Slides were coverslipped with a drop of mounting medium containing DAPI for visualization of cell nuclei (Vector Laboratories, Burlingame, Calif.).

Figure 2:
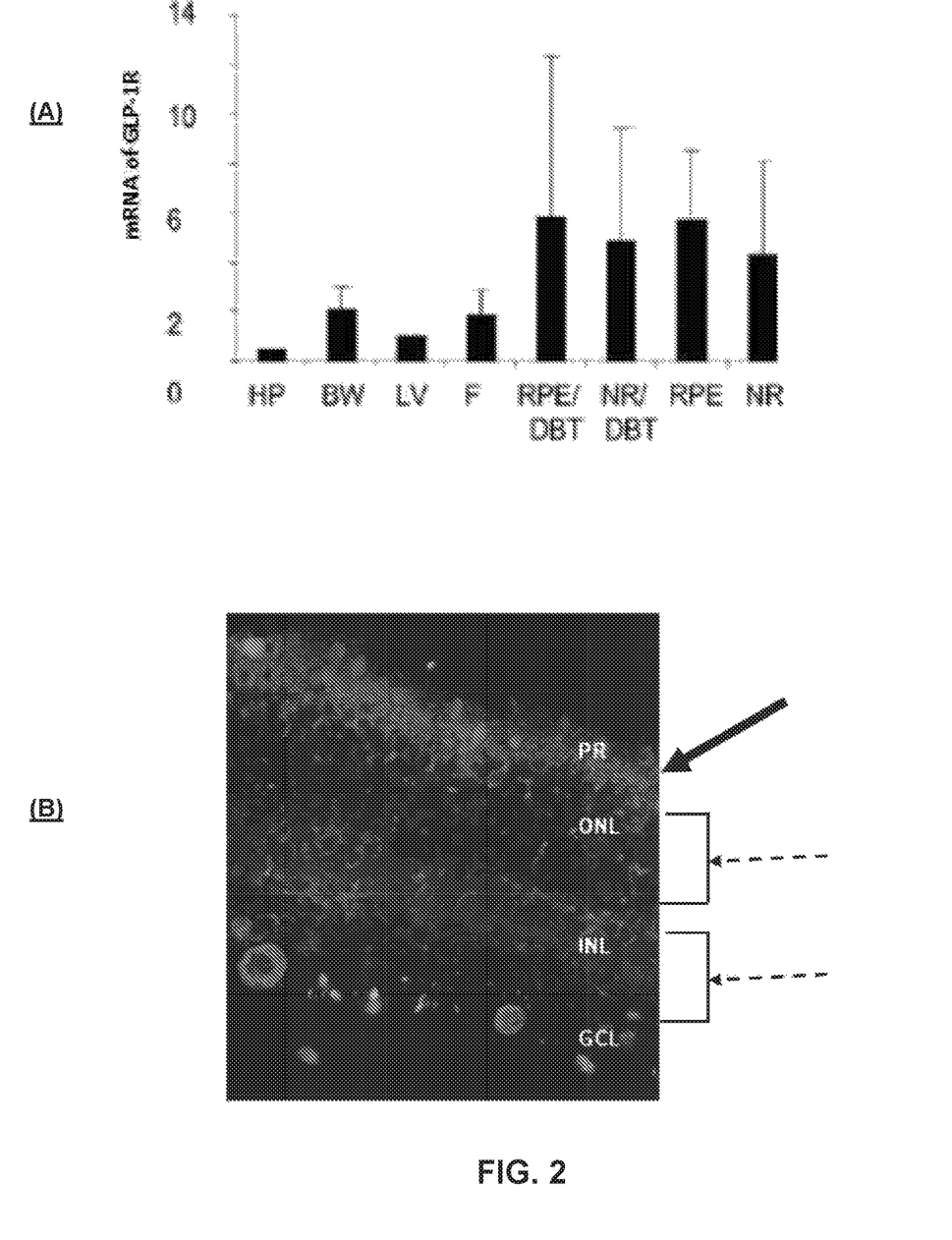

Results of the Quantitative real-time PCR (Q-RT-PCR) assay are depicted in FIG. 2A, wherein the relative quantity of the mRNA corresponding to GLP-1 receptor in several human tissues are represented. In particular the analyzed tissues were samples of retinal pigment epithelium from diabetic donors (RPE DBT), neuroretina from diabetic donors (NR DBT), retinal pigment epithelium from non-diabetic donors (RPE), neuroretina from non-diabetic donors (NR). As a comparative assay, the expression of GLP-1 receptor in other tissues were analyzed, namely in cellular line of human pancreas (HP), bowel (BW), liver (LV), and visceral fat (F). Human beta-actin was used as internal control of Q-RT-PCR.

Data in FIG. 2A demonstrated that mRNA GLP-1Rc expression could be detected in the retina from both diabetic and non-diabetic donors (RPE/DBT; NR/DBT; RPE, NR)

The results of the immunofluorescence assay are depicted in FIG. 2B, in which a 20× optical microscope image of one of the paraffinized sections is shown. The bold arrow refers to the green staining, thus corresponding to the GLP-1 receptor. Nuclei of the outer nuclear layer (ONL) are shown by means of a dashed arrow. This FIG. 2B serves to prove again that GLP-1 receptor was also detected in the retina by immunohystochemistry.

Example 2. Topical Administration of a GLP-1Rc Agonist Prevents Retinal Neurodegeneration in Diabetic Mice Animals and Treatments A total of 20 C57BL/KsJ-db/db mice obtained from Harlan Laboratories, Inc. were included. Ten C57BL/KsJ non-diabetic mice served as control group. All the experiments were performed in accordance with the protocol approved by the Animal Care and Use Committee of Vall d'Hebron Institut de Recerca (VHIR, Barcelona—Spain) and the tenets of CEE (86/609/CEE) and ARVO (Association for Research in Vision and Ophthalmology). Mice were housed under controlled conditions of temperature (20° C.) and humidity (60%) with a 12-hour light/dark cycle and had free access to food and water.

The C57BL/KsJ-db/db mice represent a good model to study the neurodegenerative features observed in patients with DR. C57BL/KsJ-db/db mice carry a mutation in the leptin receptor gene and are a model for obesity-induced type 2 diabetes. They develop hyperglycemia starting at ~4-6 weeks of age as a result of excessive food consumption.

Previous to the analysis of the effects of a GLP-1 receptor agonist, the inventors assessed the chronological sequence of the retinal abnormalities associated with diabetes. Electroretinographies and several neurodegeneration measurements including retinal morphometry, glial activation and apoptosis assessment were performed. It was concluded that total retinal thickness was significantly decreased in diabetic mice in comparison with non-diabetic mice at 16 and 24 weeks. In addition, a "reactive" diabetic phenotype characterized by hyperplasia and upregulation of the glial fibrillar acidic protein (indication of glial activation) was observed in diabetic mice. A significant increase in the number of apoptotic ganglionar cells in diabetic mice in comparison with non-diabetic mice at 8, 16 and 24 weeks was also observed. Thus, this animal model was a really good model for testing any compound directed to treating or preventing DR, and was even a better model than the one used to study retinal neurodegeneration in DR known as streptozotocin-induced diabetes (STZ-DM), in which the neurotoxic effects of the STZ can jeopardize the results.

A GLP-1Rc agonist, liraglutide, which is a GLP-1 (7-37) analogue was administered in the form of eye drops (Liraglutide, concentration: 6 mg/ml in 0.9% sodium chloride distilled water solution) directly onto the superior corneal surface of each eye using a syringe in mice 8 weeks old. As control, the vehicle (0.9% sodium chloride in water) eye drops were administered. Ten mice were treated with liraglutide and 10 mice were treated with the vehicle. The treatment (liraglutide or vehicle) was administered once daily for 14 days. On day 15, the animals' eyes were instilled with a drop of liraglutide or vehicle approximately one hour prior to necropsy. Mice were euthanized by cervical dislocation. The eyes were immediately enucleated and the neuroretina was separated. The neuroretina from one of the eyes was frozen in liquid nitrogen and stored at −80° C. for mRNA and protein assessments. The other eye was flash frozen in Tissue Freezing Medium; TFM™ (Electron Microscopy Sciences), by immersion in liquid nitrogen, and cryosectioned at 8 mm through the dorsal/ventral plane.

Sections were mounted on slides and stored at −80° C. These sections were prepared for the assessment of retinal morphology, evaluation of presence of GLP-1Rc, presence of Glial fibrilar acidic protein (GFAP) and Terminal Transfer dUTP Nick-End Labeling (TUNEL) immunoreactivity.

The assessment of GLP-1Rc presence in the neuroretinas of the mice was performed by determining the expression of mRNA by Real time-PCR, as well as by immunohistochemical and western blot analysis mRNA Expression of GLP-1Rc GLP-1Rc expression was analyzed by Real time-PCR. The following primers were used: GGGTCTCTGGCTA-CATAAGGACAAC (forward, SEQ ID NO: 6) and AAGGATGGCTGAAGCGATGAC (reverse, SEQ ID NO: 7).

Immunohistochemical Analysis

GLP-1Rc was evaluated by fluorescence microscopy using specific antibody against GLP-1Rc. Sections were fixed in acid methanol (−20° C.) for 2 min, followed by three washes in PBS, 5 min each. Sections were permeabilized with TBS-Triton X-100 0.1% and were incubated in blocker (10% BSA and 10% goat serum in PBS) for 30 min at room temperature. Sections were then incubated with GLP-1Rc (Abcam Ltd, Cambridge, U.K.) (1:500 dilution prepared in blocking solution) overnight at 4° C. in a humid atmosphere. After three washes in PBS, 5 min each, the sections were incubated with secondary antibody Alexa 594 goat-anti-rabbit (Invitrogen, UK) (1:200 dilution in prepared blocking solution). The sections were washed three times in PBS, counterstained with Hoechst and mounted with Mounting Medium Fluorescence (Prolong, Invitrogen) and mounted with a coverslip. Images were recorded with an Olympus microscope using identical brightness and contrast settings.

Western Blot Analysis:

Neuroretinas were transferred into a lysis buffer (Tris-HCl 100 mM, pH 7.5; phenylmethylsulfonyl fluoride (PMSF), 0.1 mM; Triton, 1%; NaCl, 150 mM; NaF, 20 mM; Na3PO4, 2 mM) and 1× protease inhibitors from Sigma (Sigma-Aldrich, UK) and then homogenized by syringe. The homogenates were incubated on ice for 30 minutes and were centrifuged at 10000 rpm at 4° C. for 15 minutes. The protein concentration of the supernatant was determined using BCA assay (Pierce, Thermo Scientific USA). Samples were mixed with loading buffer 6× (Tris-HCl, 1 M, pH, 6.8; sodium dodecyl sulphate (SDS), 20%; 10% Glicerol; Mercaptoetanol; and 0.01 g bromophenol blue) and boiled for ten minutes. Protein samples were resolved by 10% SDS-PAGE. After electrophoretic separation, proteins were transferred onto polyvinylidene fluoride membranes (Bio-Rad Laboratories, UK). Membranes were blocked 1 hour at room temperature in 5% non-fat powdered milk, 0.1% Tween in Tris buffered saline (TBS), and then incubated with the primary antibody against GLP-1R (1:1000 dilution; Abcam Ltd, Cambridge, UK) overnight at 4° C. Membranes were washed extensively with TBS-T (0.1% Tween) and incubated with horseradish peroxidase-labeled secondary antibody for one hour at room temperature (1:5000 dilution, Dako, Denmark). Bands were visualized using chemioluminiscence detection system (Millipore, USA). Relative protein expression was quantified by using ImageJ.

Neurodegeneration Measurements:

For determining neurodegeneration immunohistochemical analysis for glial activation assessment, as well as immunohistochemical analysis for apoptosis assessment were performed. In addition, glutamate metabolism was assessed.

Glial activation was evaluated by fluorescence microscopy using specific antibodies against GFAP (Glial fibrillar acidic protein). Sections were fixed in acid methanol (−20° C.) for 2 min, followed by three washes with PBS, 5 min each. Sections were permeabilized with TBS-Triton X-100 0.025% and were incubated in blocker (1% BSA, and 10% goat serum in PBS) for 2 hours at room temperature. Sections were then incubated with rabbit anti-GFAP (Abcam Ltd, Cambridge, U.K.) (1:500 dilution prepared in blocking solution) overnight at 4° C. in a humid atmosphere. After three washes in PBS, 5 min each, the sections were incubated with secondary antibody Alexa 488 goat-anti-rabbit (Invitrogen) (1:200 dilution prepared in blocking solution). The sections were washed three times in PBS, counterstained with Hoescht and mounted with Mounting Medium Fluorescence (Prolong, Invitrogen) and mounted with a coverslip. Comparative digital images from diabetic and control samples were recorded with an Olympus microscope using identical brightness and contrast settings.

To evaluate the degree of glial activation a scoring system based on extent of GFAP staining previously reported (Anderson et al. "Glial and endothelial blood-retinal barrier responses to amyloid-beta in the neural retina of the rat". *Clin Ophthalmol*—2008, Vol. No.: 2, pp.: 801-816) was used. The scoring system was as follows: Müller cell endfeet region/GCL only (score 1); Müller cell endfeet region/GCL plus a few proximal processes (score 2); Müller cell endfeet plus many processes, but not extending to ONL (score 3); Müller cell endfeet plus processes throughout with some in the ONL (score 4); Müller cell endfeet plus lots of dark processes from GCL to outer margin of ONL (score 5).

Apoptosis was evaluated using the TUNEL (Terminal Transferase dUTP Nick-End Labeling) method coupled with fluorescein (DeadEnd Fluorometric TUNEL System kit; PROMEGA, USA) with DAPI (4′,6-diamino-2-phenylindole) staining. Cryosections of retina were permeabilised by incubation for 2 min on ice with 0.1% Triton X-100 in 0.1% sodium citrate, freshly prepared. The secondary antibody was Alexa 594 goat-anti-rabbit (Invitrogen) (1:200 dilution prepared in blocking solution with 5% BSA). For evaluation by fluorescence microscopy an excitation wavelength in the range of 450-500 nm (e.g., 488 nm) and detection in the range of 515-565 nm (green) was used.

Glutamate accumulation in extracellular space and the overactivation of glutamate receptors ("excitotoxicity") plays an important role in retinal neurodegeneration. Glutamate transporters are essential for keeping the extracellular glutamate concentration below neurotoxic levels. Glutamate/aspartate transporter (GLAST) is the most dominant glutamate transporter, accounting for at least 50% of glutamate uptake in the mammalian retina. GLAST and glutamate were evaluated by fluorescence microscopy using specific antibodies [rabbit anti-GLAST (EAAT1) (1:100, Abcam ab416, Cambridge, UK) or rabbit anti-L glutamate (1:100, Abcam ab9440, Cambridge, UK)].

The statistical analysis of the retrieved data was made. Normal distribution of the variables was evaluated using the Kolmogorov-Smirnov test. The data were presented as mean±SD. Comparisons of continuous variables between diabetic and non-diabetic mice were performed using the unpaired Student t-test. Comparisons between categorical variables were performed by Fisher's exact test. Levels of statistical significance were set at $p<0.05$.

Results:

GLP-1Rc Expression in Mice Retina:

Although data are not shown, mRNA expression of GLP-1Rc was detected in the neuroretina of diabetic (db/db) mice as well as in non-diabetic mice (db/+) by Real Time-PCR. The expression of GLP-1Rc observed in retina was in the same range as that the observed in pancreas, a recognized target tissue for GLP-1. GLP-1Rc protein was also detected by immunohistochemistry and by Western blot analysis.

Figure 3:
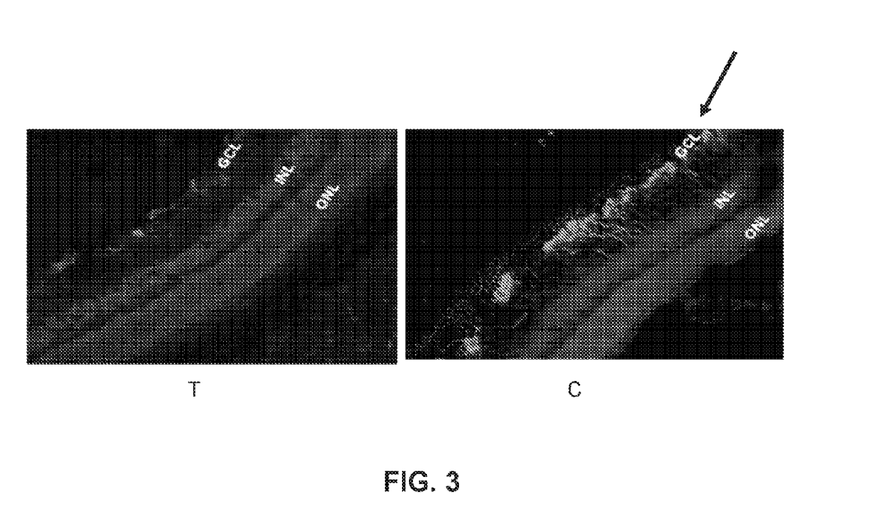
FIG. 3 related to diabetic retinopathy (DR), is a microscopic image (Olympus microscope) of retinal sections (slides), in which the presence of Glial fibrilar acidic protein (GFAP) is assessed as an indicator of glial activation. It shows a comparison of GFAP immunoreactivity (arrow) in the retina between representative samples from a diabetic mouse treated with a GLP-1(7-37) analogue, which is a GLP-1R agonist (left panel, Test, T) and a diabetic mouse treated with vehicle (right panel, Control, C). Nuclei were labeled with DAPI. ONL: outer nuclear layer; INL: inner nuclear layer; GCL: ganglion cell layer.

Data of glial activation are depicted in FIG. 3. As can be seen in FIG. 3, in the retina of diabetic mice treated with placebo (C), GFAP expression was prominent along the inner limiting membrane (INL), in Müller cell endfeet, and in Müller cell radial fibers extending through both the inner (INL) and outer retina (ONL). Diabetic mice treated with liraglutide (T) eye drops presented significantly lower GFAP immunofluorescence score than diabetic mice treated with vehicle ($p<0.05$), and similar to non-diabetic mice ($p=n.s$) (Table 1).

Next, Table 1 shows the quantification of glial activation (in percentage, %) based on scoring system (Anderson et al. Clin Ophthalmol 2008, supra).

TABLE 1

| Glial activation score | db/db mice treated with placebo (n = 10) | db/db mice treated with GLP-1Rc agonist liraglutide (n = 10) |
| --- | --- | --- |
| 1 | 4.9% | 58.5% |
| 2 | 17.1% | 39.1% |
| 3 | 46.3% | 2.4% |
| 4 | 26.8% | 0% |
| 5 | 0% | 0% |

Figure 4:
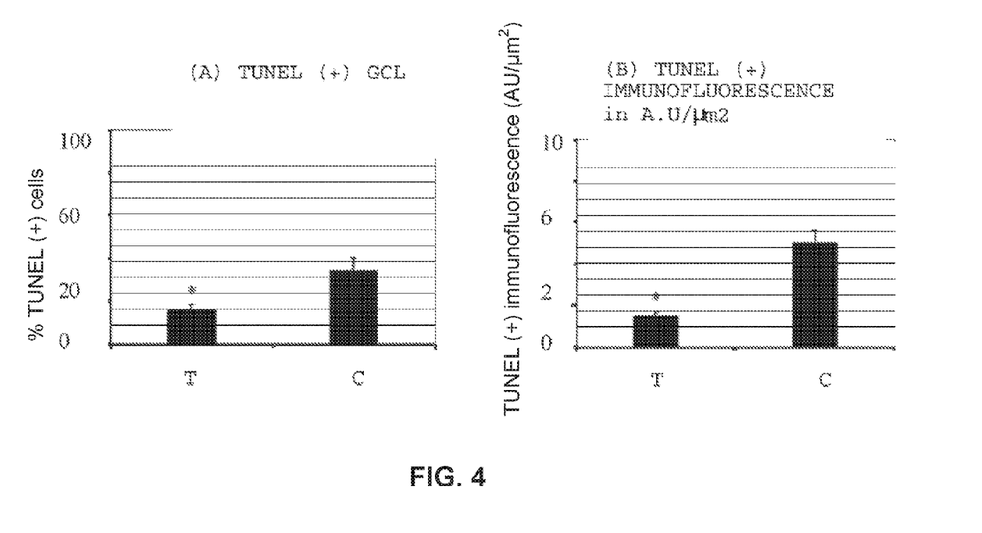

Data of retinal apoptosis assessed by TUNEL assay appear in FIG. 4. wherein in panel A the percentage of TUNEL positive cells in the Ganglion cell layer (GCL) in diabetic mice treated with the GLP-1(7-37) analogue liraglutide, (T, n=10) and in diabetic mice treated with vehicle (Control, C, n=10) is shown. The data are also depicted in panel B for the TUNEL positive immunofluorescence in neuroretina from diabetic mice treated with the GLP-1R agonist (T) and for diabetic mice treated with vehicle (Control, C). In this panel B it is depicted in arbitrary units the quantification of the TUNEL fluorescence in the whole retina (neuroretina) A.U.: arbitrary units. Results are mean±SD. * $p<0.05$.

As can be seen in FIG. 4, the whole percentage of retinal apoptotic cells in the whole retina, as well as the percentage of apoptotic cells in retinal layers (outer nuclear layer, inner nuclear layer and ganglion cells layer) was significantly higher in comparison to that observed in retinas from age-matched non-diabetic controls ($p<0.01$). In all groups apoptosis was highest in the ganglion cell layer. Diabetic mice treated with the GLP-1Rc agonist (liraglutide) presented a significantly lower ratio of apoptosis in the ganglion cell layer than diabetic mice treated with placebo ($p<0.05$). Furthermore, diabetic mice treated with GLP-1Rc agonist eye drops presented significantly lower TUNEL+immunofluorescence intensity than diabetic mice treated with vehicle, and similar to non-diabetic mice ($p=n.s$). Thus, in treated mice there were lower levels of apoptotic cells, which is an indirect measure of lower retinal damage.

Figure 5:
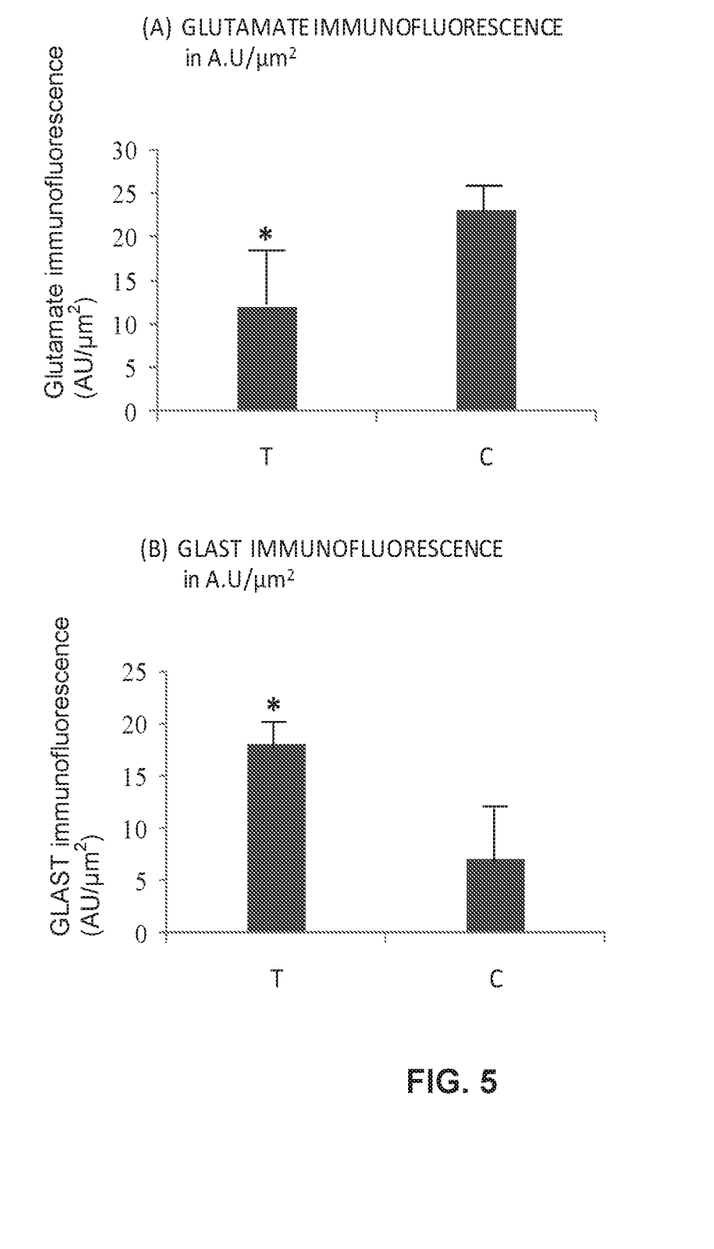
FIG. 5 also related to diabetic retinopathy (DR), is a bar diagram showing the results of glutamate immunofluorescence (Panel A) and GLAST immunofluorescence (Panel B) in the whole neuroretina from diabetic mice treated with GLP-1R agonist (T) and diabetic mice treated with vehicle (Control, C). A.U.: arbitrary units. Results are mean±SD. * p<0.05.

The increase of glutamate levels caused by diabetes (C) was abrogated in diabetic mice treated with the GLP-1Rc agonist (T). This beneficial effect was associated with a significant increase in GLAST content in diabetic mice treated with the GLP-1Rc agonist (T) (FIG. 5).

All these data taken together provide first evidence that topical ocular administration (eye drops) of GLP-1Rc agonists has a potent effect in preventing the retinal neurodegenerative process that occurs in the early stages of diabetic retinopathy. The data also provide evidence that other retinal diseases in which neurodegeneration plays an essential role may be treated and/or prevented with the topical ocular administration (eye drops) of GLP-1Rc agonists, in particular with the topical administration of the peptides as above disclosed.

REFERENCES CITED IN THE APPLICATION

Schmidt et al., "Neurodegenerative Diseases of the Retina and Potential for the Protection and Recovery", *Current Neuropharmacoloqy*—2008, Vol. No. 6, pp.: 164-178.
Simo et al., "Neurodegeneration is an early event in diabetic retinopathy: therapeutic implications", *Br. J. Ophthalmol.*—2012, vol. 96, pp. 1285-1290 Aiello et al., "Targeting Intraocular Neovascularization and Edema—One Drop at a Time", *N. Eng. J Med*—2008, vol. 359, pp. 967-969.
Urtti A et al., "Challenges and obstacles of ocular pharmacokinetics and drug delivery". *Adv. Drug. Deliv. Rev.* 2006, vol. 58, pp. 1131-1135.
WO2007062434
Zhang et al., "Intravitreal injection of exendin-4 analogue protects retinal cells in early diabetic rats", Invest Ophthalmol Vis Sci.—2011, vol. 52(1), pp.: 278-85.
EP0944648.
U.S. Pat. No. 5,424,286
Carrasco et al., "Lower Somatostatin Expression Is an Early Event in Diabetic Retinopathy and Is Associated With Retinal Neurodegeneration", *Diabetes Care*—2007, Vol. No. 30, pp.: 2902-2908
Anderson et al. "Glial and endothelial blood-retinal barrier responses to amyloid-beta in the neural retina of the rat". *Clin Ophthalmol*—2008, Vol. No.: 2, pp.: 801-816.

The invention claimed is:

1. A method for the treatment of retinal neurodegenerative disease comprising topically administering onto the eye surface a therapeutically effective amount of a peptide with a sequence length from 13 to 50 amino acids, the N-terminal region of said peptide having the sequence:

HXaa$^1$EGTFTSDXaa$^2$SXaa$^3$Xaa$^4$ (SEQ ID NO: 1)

wherein:
Xaa$^1$ is an amino acid selected from alanine and glycine;
Xaa$^2$ is an amino acid selected from valine and leucine;
Xaa$^3$ is an amino acid selected from serine and lysine;
Xaa$^4$ is an amino acid selected from tyrosine and glutamine; and
hystidine is the N-terminal residue;
together with pharmaceutically acceptable excipients and/or carriers, in a subject in need thereof.

2. The method of claim 1, wherein the peptide has a sequence length from 30 to 40 amino acids.

3. The method of claim 1, wherein the retinal neurodegenerative disease is selected from the group consisting of diabetic retinopathy (DR), age-related macular degeneration, glaucoma and retinitis pigmentosa.

4. The method of claim 1, wherein the retinal neurodegenerative disease is diabetic retinopathy.

5. The method of claim 4, which is a topical treatment of early stages of the diabetic retinopathy.

6. The method of claim 4, comprising topically administering onto the eye surface a therapeutically effective amount of a peptide selected from:
  (a) the human glucagon-like peptide-1 (7-37) of amino acid sequence SEQ ID NO: 2;
  (b) the amino acid sequence SEQ ID NO: 3 (HAEGTFTSDVSSYLEGQAAKEFIAWLVRGRG), wherein the lysine residue (K) comprises the lipophilic substituent $N^\epsilon$-($\gamma$-glutamyl($N^\alpha$-hexadecanoyl)) attached by an amide link to the amino group of the lysine side chain;
  (c) the amino acid sequence SEQ ID NO: 4 (HGEGTFTSDLSKQMEEEAVRLFIEWLKNGGPSSGAPPPXaa$^5$), wherein Xaa$^5$ is a serine residue in which the —COOH terminal has been replaced by a —NH$_2$ group; and
  (d) the amino acid sequence SEQ ID NO: 8 (HGEGTFTSDLSKQMEEEAVRLFIEWLKNGGPSSGAPPSKKKKKXaa$^6$), wherein Xaa$^6$ is a lysine residue in which the —COOH terminal has been replaced by a —NH$_2$ group.

7. The method of claim 5, comprising topically administering onto the eye surface a therapeutically effective amount of a peptide selected from:
  (a) the human glucagon-like peptide-1 (7-37) of amino acid sequence SEQ ID NO: 2;
  (b) the amino acid sequence SEQ ID NO: 3 (HAEGTFTSDVSSYLEGQAAKEFIAWLVRGRG), wherein the lysine residue (K) comprises the lipophilic substituent $N^\epsilon$-($\gamma$-glutamyl($N^\alpha$-hexadecanoyl)) attached by an amide link to the amino group of the lysine side chain;
  (c) the amino acid sequence SEQ ID NO: 4 (HGEGTFTSDLSKQMEEEAVRLFIEWLKNGGPSSGAPPPXaa$^5$), wherein Xaa$^5$ is a serine residue in which the —COOH terminal has been replaced by a —NH$_2$ group; and
  (d) the amino acid sequence SEQ ID NO: 8 (HGEGTFTSDLSKQMEEEAVRLFIEWLKNGGPSSGAPPSKKKKKXaa$^6$), wherein Xaa$^6$ is a lysine residue in which the —COOH terminal has been replaced by a —NH$_2$ group.

8. The method of claim 1, in which Xaa$^1$ is alanine, Xaa$^2$ is valine, Xaa$^3$ is serine, and Xaa$^4$ is tyrosine.

9. The method of claim 1, comprising topically administering onto the eye surface a therapeutically effective amount of a mammal glucagon-like peptide-1.

10. The method of claim 9, comprising topically administering onto the eye surface a therapeutically effective amount of the human glucagon-like peptide-1 (7-37) of amino acid sequence SEQ ID NO: 2.

11. The method of claim 1, comprising topically administering onto the eye surface a therapeutically effective amount of the amino acid sequence SEQ ID NO: 3:
  HAEGTFTSDVSSYLEGQAAKEFIAWLVRGRG,
  wherein the lysine residue (K) comprises the lipophilic substituent $N^\epsilon$-($\gamma$-glutamyl($N^\alpha$-hexadecanoyl)) attached by an amide link to the amino group of the lysine side chain.

12. The method of claim 1, in which Xaa$^1$ is glycine, Xaa$^2$ is leucine, Xaa$^3$ is lysine, and Xaa$^4$ is glutamine.

13. The method of claim 12, comprising topically administering onto the eye surface a therapeutically effective amount of the amino acid sequence SEQ ID NO: 4:
  HGEGTFTSDLSKQMEEEAVRLFIEWLKNGGPSSGAPPPXaa$^5$,
  wherein
  Xaa$^5$ is a serine residue in which the —COOH terminal has been replaced by a —NH$_2$ group.

14. The method of claim 12, comprising topically administering onto the eye surface a therapeutically effective amount of the amino acid sequence SEQ ID NO: 8:
  HGEGTFTSDLSKQMEEEAVRLFIEWLKNGGPSSGAPPSKKKKKXaa$^6$
  wherein
  Xaa$^6$ is a lysine residue in which the —COOH terminal has been replaced by a —NH$_2$ group.

15. The method of claim 1, wherein the subject is a human.

16. A method for the treatment of a retinal neurodegenerative disease comprising topically administering onto the eye surface a therapeutically effective amount of a pharmaceutical topical composition comprising a peptide with a sequence length from 13 to 50 amino acids, the N-terminal region of said peptide having the sequence:
  HXaa$^1$EGTFTSDXaa$^2$SXaa$^3$Xaa$^4$ (SEQ ID NO: 1)
  wherein;
  Xaa$^1$ is an amino acid selected from alanine and glycine;
  Xaa$^2$ is an amino acid selected from valine and leucine;
  Xaa$^3$ is an amino acid selected from serine and lysine;
  Xaa$^4$ is an amino acid selected from tyrosine and glutamine; and
  hystidine is the N-terminal residue;
  together with pharmaceutically acceptable excipients and/or carriers, in a subject in need thereof.

17. The method of claim 16, wherein the pharmaceutical topical composition is selected from the group consisting of solutions, creams, lotions, unguents, emulsions, and suspensions.

18. The method of claim 16, wherein the pharmaceutical topical composition is an eye drop solution.

19. The method of claim 16, wherein the retinal neurodegenerative disease is selected from the group consisting of diabetic retinopathy, age-related macular degeneration, glaucoma and retinitis pigmentosa.

20. The method of claim 16, wherein the retinal neurodegenerative disease is diabetic retinopathy.

21. The method of claim 16, wherein the subject is a human.

* * * * *